(12) United States Patent
Uehara et al.

(10) Patent No.: US 8,592,018 B2
(45) Date of Patent: Nov. 26, 2013

(54) TUBE AND MEDICAL DEVICE USING SAME

(75) Inventors: Yosuke Uehara, Okayama (JP);
Nobuhiro Moriguchi, Okayama (JP);
Shigenao Kuwahara, Ibaraki (JP);
Hidetaka Oonuma, Ibaraki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 13/255,174

(22) PCT Filed: Mar. 9, 2010

(86) PCT No.: PCT/JP2010/053874
§ 371 (c)(1),
(2), (4) Date: Sep. 7, 2011

(87) PCT Pub. No.: WO2010/104068
PCT Pub. Date: Sep. 16, 2010

(65) Prior Publication Data
US 2011/0319837 A1 Dec. 29, 2011

(30) Foreign Application Priority Data
Mar. 9, 2009 (JP) .................. 2009-055350

(51) Int. Cl.
C08L 23/10 (2006.01)
C08L 53/02 (2006.01)
A61L 29/04 (2006.01)

(52) U.S. Cl.
USPC ................ 428/36.9; 428/36.92; 525/95

(58) Field of Classification Search
USPC ................ 525/88, 95; 428/36.9, 36.92
See application file for complete search history.

(56) References Cited

U.S. PATENT DOCUMENTS

| | | | | |
|---|---|---|---|---|
| 6,977,105 B1 * | 12/2005 | Fujieda et al. | ............... | 428/36.9 |
| 2002/0104544 A1 * | 8/2002 | Ogushi et al. | ........... | 128/207.14 |
| 2005/0048271 A1 * | 3/2005 | Iwasa et al. | ................ | 428/195.1 |
| 2008/0215016 A1 | 9/2008 | Igarashi et al. | | |
| 2010/0239802 A1 * | 9/2010 | Kuwahara et al. | ........... | 428/36.9 |

FOREIGN PATENT DOCUMENTS

| | | |
|---|---|---|
| JP | 4 159344 | 6/1992 |
| JP | 10 67894 | 3/1998 |
| JP | 10 306181 | 11/1998 |
| JP | 2002 248671 | 9/2002 |
| JP | 2002 327872 | 11/2002 |
| WO | 2006 057370 | 6/2006 |
| WO | 2006 134974 | 12/2006 |
| WO | 2009/031625 | * 3/2009 |

OTHER PUBLICATIONS

International Search Report Issued Apr. 6, 2010 in PCT/JP10/053874 filed Mar. 9, 2010.

* cited by examiner

Primary Examiner — Jeffrey Mullis
(74) Attorney, Agent, or Firm — Oblon, Spivak, McClelland, Maier & Neustadt, L.L.P.

(57) ABSTRACT

Provided are a tube which has good transparency, flexibility, and solvent adhesion, and also has excellent clamp resistance, anti-conglutination property, and kink resistance, and a medical device using the tube. Specifically provided are a tube produced by forming a resin composition into a tube shape, which contains a styrene-based thermoplastic elastomer (a) and a polypropylene-based resin (b) and does not contain a softening agent, in which: the elastomer (a) is a product prepared by hydrogenating a block copolymer including at least a polymer block (A) formed of an aromatic vinyl compound and a polymer block (B) formed of isoprene and/or 1,3-butadiene; the content of the polymer block (A) is 5 to 40 mass % before hydrogenation, the polymer block (B) has a hydrogenation ratio of 70% or more, and the polymer block (B) includes a 1,2-bond and a 3,4-bond at a content of 30 to 85 mol %; the mass ratio of the styrene-based thermoplastic elastomer (a) to the polypropylene-based resin (b) [(a)/(b)] is 90/10 to 40/60; and the tube has a ratio of a diffraction peak intensity [I(14)] at a scattering angle of 14° to a diffraction peak intensity [I(15)] at a scattering angle of 15° [I(14)/I(15)] of 1.4 or more in X-ray diffraction, and a medical device including the tube.

42 Claims, 1 Drawing Sheet

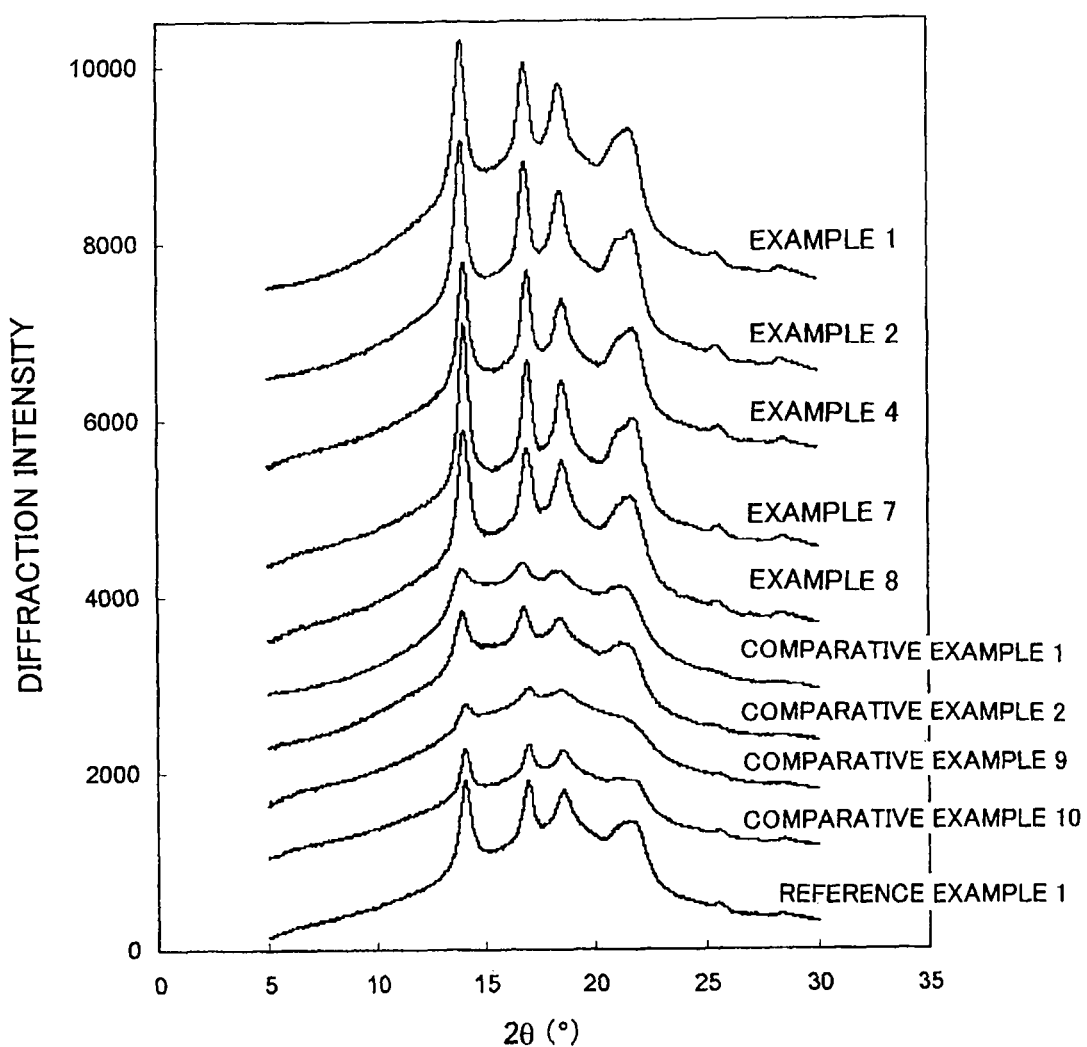

TUBE AND MEDICAL DEVICE USING SAME

This application is a U.S. national-stage application under 35 U.S.C. §371 of PCT/JP10/053874 filed Mar. 9, 2010. Priority is also claimed to Japan 2009-055350, filed Mar. 9, 2009.

TECHNICAL FIELD

The present invention relates to a tube which has good transparency, flexibility, and solvent adhesion, and also has excellent clamp resistance, anti-conglutination property, and kink resistance, and to a medical device using the tube.

BACKGROUND ART

Conventionally, a medical tube used for a catheter, an infusion bag, a blood bag, or the like has been often manufactured by using soft vinyl chloride resin excellent in tube characteristics such as flexibility, transparency, kink resistance, and clamp resistance. However, it has been pointed out that soft vinyl chloride resin has a safety problem in that a plasticizer having a lower molecular weight is eluted, and has an environmental problem in that a toxic gas is produced at the time of its disposal and incineration.

Thus, in order to avoid the above-mentioned problems, the applicant proposed, as a resin composition having flexibility and being suitable for medical application, a resin composition produced by blending a polypropylene-based resin with a hydrogenated elastomer of a block copolymer containing a polymer block formed of an aromatic vinyl compound and a conjugated diene-based polymer block (see Patent Literature 1).

A tube made from this thermoplastic elastomer has had transparency and flexibility, but has had points to be improved in kink resistance, clamp resistance, and anti-conglutination property.

In order to improve kink resistance, it is known to produce a tube by blending a polyolefin-based resin with a specific hydrogenated styrene-based thermoplastic elastomer, a softening agent, and the like (see Patent Literatures 2 and 3). As far as anti-conglutination property concerned, there is known a soft polymer composition including a block copolymer formed of polystyrene and an ethylene-propylene copolymer, a block copolymer formed of polystyrene and an ethylene-butylene copolymer, and a polyolefin (see Patent Literature 4).

Further, in order for a tube to have a plurality of characteristics, which are required to serve as a good tube, it is known to adopt a multilayered tube having a surface resin layer and an inner resin layer formed of different compositions (see Patent Literatures 5 and 6).

In addition, there is known a tube for medical purpose including a resin composition produced by blending (a) a hydrogenated block copolymer prepared by hydrogenating a polymer block formed of a vinyl aromatic compound and a polymer block formed of a conjugated diene, (b) an olefin-based copolymer, and (c) a hydrocarbon-based softening agent for a rubber (see Patent Literature 7).
[Patent Literature 1] JP 10-67894 A
[Patent Literature 2] JP 2002-248671 A
[Patent Literature 3] JP 2003-287163 A
[Patent Literature 4] JP 04-159344 A
[Patent Literature 5] JP 2001-1432 A
[Patent Literature 6] JP 2004-194803 A
[Patent Literature 7] WO 2006/134974 A1

DISCLOSURE OF THE INVENTION

Problems that the Invention is to Solve

By adopting any of the compositions and tubes described in Patent Literatures 1 to 7, there has been obtained a tube having flexibility similar to that of soft vinyl chloride resin, but it has been difficult to obtain a tube having clamp resistance, anti-conglutination property, and kink resistance, which are important as tube characteristics. For example, in the endotracheal tube described in Patent Literature 2, no satisfactory improvement has been found in deformation, dent, and the like of the tube, and hence any tube having clamp resistance and kink resistance has not been provided. Further, when a softening agent was blended in a tube to improve its kink resistance as described in Patent Literatures 3 and 7, there have been problems with clamp resistance and conglutination of tubes to each other.

When the composition described in Patent Literature 4 was used to produce a tube, the anti-conglutination property of the tube has improved, but its kink resistance has not been sufficient and its transparency has been insufficient. The multilayered tubes described in Patent Literatures 5 and 6 are formed by co-extrusion, and hence each of their production processes is complicated, leading to high production cost, and moreover, it is not easy to control the thickness of each layer uniformly. In addition, even though adopting a multilayered tube improved the clamp resistance and anti-conglutination property of the tube, there has been a problem sometimes in that the solvent adhesion of the surface layer of the tube with a connection member is poor, and sufficient adhesive strength is not provided.

Under the circumstances described above, there has been demanded, particularly for medical application, a tube having excellent clamp resistance, anti-conglutination property, and kink resistance.

An object of the present invention is to provide a tube which has good transparency, flexibility, and solvent adhesion, and also has excellent clamp resistance, anti-conglutination property, and kink resistance, the properties being required for a tube, and a medical device using the tube.

Note that herein, the term "kink resistance" refers to the property of being resistant to abnormal deformation such as buckling which occurs when a tube is bent so as to have a ring shape or an arc shape, the term "clamp resistance" refers to such property that, when a tube is clamped with a medical clamp, the inner surfaces of the tube are not conglutinated to each other, and when the medical clamp is removed from the tube, the tube immediately recovers its original shape, and the term "solvent adhesion" refers to such property that, when a tube is connected to connectors with a solvent, sufficient adhesive strength is provided to the connection.

Means for Solving the Problems

The present invention provides the following items (1) and (2).
(1) A tube produced by forming a resin composition into a tube shape, which contains a styrene-based thermoplastic elastomer (a) and a polypropylene-based resin (b) and does not contain a softening agent, in which: the styrene-based thermoplastic elastomer (a) is a hydrogenated block copolymer prepared by hydrogenating a block copolymer including at least a polymer block (A) formed of an aromatic vinyl compound and a polymer block (B) formed of isoprene and/or 1,3-butadiene; the content of the polymer block (A) is 5 to 40 mass % with respect to the total amount of the styrene-based thermoplastic elastomer (a) before hydrogenation, the polymer block (B) has a hydrogenation ratio of 70% or more, and the polymer block (B) includes a 1,2-bond and a 3,4-bond at a content of 30 to 85 mol %; a mass ratio of the styrene-based thermoplastic elastomer (a) to the polypropylene-based resin (b), that is, [(a)/(b)], is 90/10 to 40/60; and the tube has a ratio of a diffraction peak intensity [I(14)] at a scattering angle (2θ) of 14° to a diffraction peak intensity [I(15)] at a scattering angle (2θ) of 15°, that is, [I(14)/I(15)], of 1.4 or more in wide-angle X-ray diffraction. (2) A medical device, including the tube according to the item (1).

Advantage of the Invention

According to the present invention, the tube which has good transparency, flexibility, and solvent adhesion, and also has excellent clamp resistance, anti-conglutination property, and kink resistance, and the medical device using the tube can be provided.

BRIEF DESCRIPTION OF DRAWING

FIG. 1 shows wide-angle X-ray diffraction patterns of tubes produced in examples, comparative examples, and a reference example.

BEST MODE FOR CARRYING OUT THE INVENTION

A tube of the present invention is produced by forming a resin composition into a tube shape, which includes a styrene-based thermoplastic elastomer (a) and a polypropylene-based resin (b).

<Styrene-Based Thermoplastic Elastomer (A)>

The styrene-based thermoplastic elastomer (a) is a hydrogenated block copolymer prepared by hydrogenating a block copolymer including at least a polymer block (A) formed of an aromatic vinyl compound and a polymer block (B) formed of isoprene and/or 1,3-butadiene, in which the content of the polymer block (A) is 5 to 40 mass % with respect to the total amount of the styrene-based thermoplastic elastomer (a) before hydrogenation, the polymer block (B) has a hydrogenation ratio of 70% or more, and the polymer block (B) includes a 1,2-bond and a 3,4-bond at a content of 30 to 85 mol %.

In order to obtain a resin composition to be formed into a tube having clamp resistance, anti-conglutination property, and kink resistance, it is important to control the structure of the styrene-based thermoplastic elastomer (a) to such structure as described above. Described hereinafter are specific examples and the like of the polymer block (A) and the polymer block (B) both that form the styrene-based thermoplastic elastomer (a) and those of the styrene-based thermoplastic elastomer (a).

[Polymer Block (A)]

The polymer block (A) in the styrene-based thermoplastic elastomer (a) mainly includes a structural unit derived from an aromatic vinyl compound. Here, the term "mainly" means that the content of the aromatic vinyl compound unit is, with respect to the mass of the polymer block (A), preferably 80 mass or more, more preferably 90 mass % or more, still more preferably 100 mass %.

Examples of the aromatic vinyl compound that forms the polymer block (A) include styrene, α-methylstyrene, β-methylstyrene, o-methylstyrene, m-methylstyrene, p-methylstyrene, 4-propylstyrene, 4-cyclohexylstyrene, 4-dodecylstyrene, 2-ethyl-4-benzylstyrene, 4-(phenylbutyl)styrene, t-butylstyrene, 2,4,6-trimethylstyrene, monofluorostyrene, difluorostyrene, monochlorostyrene, dichlorostyrene, methoxystyrene, 1-vinylnaphthalene, 2-vinylnaphthalene, vinylanthracene, indene, and acetonaphthylene.

The polymer block (A) may include only a structural unit derived from one kind of the aromatic vinyl compounds described above, or may include structural units derived from two or more kinds thereof. In particular, it is preferred that the polymer block (A) mainly include a structural unit derived from styrene, α-methylstyrene, or p-methylstyrene, and it is more preferred that the polymer block (A) mainly include a structural unit derived from styrene.

The polymer block (A) may include a small amount of a structural unit derived from any other copolymerizable monomer together with the structural unit derived from the aromatic vinyl compound. In this case, the content ratio of the structural unit derived from the other copolymerizable monomer is, with respect to the mass of the aromatic vinyl polymer block, preferably 20 mass % or less, more preferably 10 mass % or less.

Examples of the other copolymerizable monomer include ionically polymerizable monomers such as 1-butene, pentene, hexene, 1,3-butadiene, isoprene, 2,3-dimethyl-1,3-butadiene, 1,3-pentadiene, 1,3-hexadiene, and methyl vinyl ether.

[Polymer Block (B)]

The polymer block (B) in the styrene-based thermoplastic elastomer (a) mainly includes a structural unit derived from isoprene and/or 1,3-butadiene. Here, the term "mainly" means that the content of the isoprene unit and/or the 1,3-butadiene unit is, with respect to the mass of the polymer block (B), preferably 80 mass % or more, more preferably 90 mass % or more, still more preferably 100 mass %.

When the polymer block (B) mainly includes a mixed unit of the 1,3-butadiene unit and the isoprene unit, the mixture ratio between the 1,3-butadiene unit and the isoprene unit is not particularly limited. Further, the polymerization form of 1,3-butadiene and isoprene is not particularly limited, and can be selected from a random copolymer, a tapered copolymer, a block copolymer, a copolymer having a partial block structure, and a combination of two or more kinds thereof.

The polymer block (B) may include a small amount of a structural unit derived from any other copolymerizable monomer together with the structural unit derived from isoprene and/or 1,3-butadiene. In this case, the content ratio of the structural unit derived from the other copolymerizable monomer is, with respect to the mass of the polymer block (B), preferably 20 mass % or less, more preferably 10 mass % or less.

Examples of the other copolymerizable monomer include: aromatic vinyl compounds such as styrene, α-methylstyrene, β-methylstyrene, o-methylstyrene, m-methylstyrene, p-methylstyrene, 4-propylstyrene, 4-cyclohexylstyrene, 4-dodecylstyrene, 2-ethyl-4-benzylstyrene, 4-(phenylbutyl)styrene, t-butylstyrene, 2,4,6-trimethylstyrene, monofluorostyrene, difluorostyrene, monochlorostyrene, dichlorostyrene, methoxystyrene, 1-vinylnaphthalene, 2-vinylnaphthalene, vinylanthracene, indene, and acetonaphthylene; and ionically polymerizable monomers such as 1-butene, pentene, hexene, 2,3-dimethyl-1,3-butadiene, 1,3-pentadiene, 1,3-hexadiene, and methyl vinyl ether.

The hydrogenation ratio of the polymer block (B), that is, the hydrogenation ratio of the carbon-carbon double bonds in the structural unit derived from isoprene and/or 1,3-butadiene included in the polymer block (B), should be 70% or more, and is preferably 80% or more, more preferably 85% or more. When the hydrogenation ratio of the polymer block (B) in the styrene-based thermoplastic elastomer (a) is less than 70%, the transparency of a tube produced from the resultant resin composition tends to lower.

Note that the hydrogenation ratio is calculated by measuring the iodine values of the block copolymer before and after hydrogenation reaction.

The bonding form of isoprene and/or 1,3-butadiene in the polymer block (B) includes an 1,4-bond, and in addition to that, the bonding form of isoprene can include a 3,4-bond and an 1,2-bond, and the bonding form of 1,3-butadiene can include an 1,2-bond.

Of those, the content of the 1,2-bond and the 3,4-bond (degree of vinylation) in the polymer block (B) is, with respect to the structural unit derived from isoprene and/or 1,3-butadiene in the polymer block (B), should be in the range of 30 to 85 mol %, is preferably in the range of 45 to 80 mol %, more preferably in the range of 55 to 70 mol %. If the content of the 1,2-bond and the 3,4-bond in the polymer block (B) is less than 30 mol %, the transparency of a tube produced from the resultant resin composition may lower. On the other hand, if the content is more than 85 mol %, the flexibility of a tube produced from the resultant resin composition may lower. Thus, both cases are not preferred.

The glass transition temperature of the polymer block (B) is preferably −50 to 30° C., more preferably −50 to 10° C., more preferably −45 to 10° C., still more preferably −40 to 0° C. If the glass transition temperature of the polymer block (B) is less than −50° C., the transparency of a tube produced from the resultant resin composition may lower. If the glass transition temperature is more than 30° C., the flexibility of a tube produced from the resultant resin composition may lower. Thus, both cases are not preferred.

Note that the glass transition temperature means the glass transition temperature measured at a rate of temperature increase of 10° C./minute by using a differential scanning calorimeter.

The styrene-based thermoplastic elastomer (a) to be used in the present invention is a hydrogenated block copolymer including at least one kind of each of the polymer block (A) and the polymer block (B). The bonding form between the polymer block (A) and the polymer block (B) is not particularly limited, and may be any bonding form selected from a linear form, a branched form, a radial form, and a combination of two or more thereof.

The content of the polymer block (A) should be 5 to 40 mass %, with respect to the total amount of the styrene-based thermoplastic elastomer (a) before hydrogenation, is preferably 5 to 30 mass %, more preferably 5 to 20 mass %, still more preferably 5 to 10 mass %. If the content of the polymer block (A) is less than 5 mass %, the mechanical strength of a tube produced from the resultant resin composition may lower. On the other hand, if the content is more than 40 mass %, the transparency of a tube produced from the resultant resin composition tends to lower.

Further, the content of the polymer block (A) is particularly preferably 5 to 10 mass %, because a tube produced from the resultant resin composition is excellent in kink resistance and flexibility.

The kink resistance is influenced by the anisotropy of a tube between the machine direction (MD) and the transverse direction (TD) perpendicular thereto. Thus, as the ratio of the moduli of elasticity (M) of the respective directions, [M(MD)/M(TD)], becomes smaller in a tube, the tube has better kink resistance. When the content of the polymer block (A) is controlled to 10 mass % or less in the present invention, the [M(MD)/M(TD)] of the resultant tube becomes smaller, and hence the tube has better kink resistance.

Further, if the forming speed of a tube is increased for the purpose of increasing its productivity, the shear force applied to the tube during the forming becomes stronger, resulting in the increase of the anisotropy of the tube. Thus, the [M(MD)/M(TD)] of the resultant tube becomes larger, and consequently, the kink resistance of the tube tends to lower. However, by using a styrene-based thermoplastic elastomer (a) which contains the polymer block (A) at a content of 10 mass % or less, the [M(MD)/M(TD)] of the resultant tube becomes smaller irrespective of the forming speed of the tube, and hence the tube exhibits excellent kink resistance.

[Specific Examples of Styrene-Based Thermoplastic Elastomer (a)]

Specific examples of the styrene-based thermoplastic elastomer (a) include, when the polymer block formed of an aromatic vinyl compound is represented by A and the polymer block formed of isoprene and/or 1,3-butadiene is represented by B, a diblock copolymer represented by [A-B], a triblock copolymer represented by [A-B-A] or [B-A-B], a tetrablock copolymer represented by [A-B-A-B] or [B-A-B-A], a polyblock copolymer in which five or more A's and B's in total are linked linearly, a (A-B)nX type copolymer (X represents a coupling residue and n represents an integer of 3 or more), and mixtures thereof. Of those, a triblock copolymer represented by [A-B-A] is preferred, from the standpoint of the characteristics of the tube produced from the resultant resin composition and its ease of handling.

Herein, when polymer blocks of the same kind are linked linearly via a divalent coupling agent or the like, the whole linked polymer block is treated as one polymer block. Thus, a polymer block that should be strictly represented fundamentally as [A-X-A], including the above-mentioned exemplification, is represented as A altogether, except the case that the polymer block [A-X-A] needs to be particularly distinguished from the single polymer block A. Herein, the polymer block of this kind including a coupling agent residue is treated as described above, and hence, for example, a block copolymer that includes a coupling agent residue and should be strictly represented as [A-B-X-B-A] is represented as [A-B-A] and is treated as one example of triblock copolymers.

The molecular weight of each of the polymer block (A) and the polymer block (B) in the styrene-based thermoplastic elastomer (a) is not particularly limited. From the standpoint of the mechanical properties, forming processability, and the like of the tube produced from the resultant resin composition, the weight average molecular weight of the polymer block (A) is preferably 1,500 to 100,000, and the weight average molecular weight of the polymer block (B) is preferably 2,500 to 400,000.

Besides, the weight average molecular weight of the styrene-based thermoplastic elastomer (a) in total is, from the standpoint of the mechanical properties, forming processability, and the like of the tube produced from the resultant resin composition, preferably 4,000 to 500,000, more preferably 30,000 to 300,000, still more preferably 50,000 to 250,000.

Note that the weight average molecular weight herein refers to a value obtained on the basis of the measurement value of a styrene-based thermoplastic elastomer after hydrogenation with a gel permeation chromatography (GPC) method with reference to a standard polystyrene calibration curve.

Examples of the styrene-based thermoplastic elastomer (a) include a block copolymer having the structure of a [A1-B-A2] type, which includes a polymer block (A1) and a polymer block (A2) each formed of an aromatic vinyl compound and the polymer block (B) formed of isoprene and/or 1,3-butadiene. In this case, when the weight average molecular weight of the polymer block (A1) is represented by [Mw(A1)] and the weight average molecular weight of the polymer block (A2) is represented by [Mw (A2)], their ratio [Mw(A1)/Mw(A2)] is, from the standpoint of the fluidity of the resultant resin composition and the transparency and flexibility of the tube produced from the resin composition, preferably 0.10 to 1.00, more preferably 0.20 to 1.00, still more preferably 0.25 to 1.00, still more preferably 0.25 to 0.60, still more preferably 0.25 to 0.50.

[Production of Block Copolymer]

A method of producing the block copolymer is not particularly limited, and any known method can be used for its production. For example, the block copolymer may be produced by any of an ionic polymerization method such as anionic polymerization or cationic polymerization, a single-site polymerization method, a radical polymerization method, and the like. Examples of the anionic polymerization method include the following methods (i) to (iii).

(i) A method in which an aromatic vinyl compound, isoprene and/or 1,3-butadiene, and an aromatic vinyl compound are sequentially polymerized by using an alkyllithium compound as a polymerization initiator.

(ii) A method in which an aromatic vinyl compound and isoprene and/or 1,3-butadiene are sequentially polymerized by using an alkyllithium compound as a polymerization initiator, followed by addition of a coupling agent for inducing coupling.

(iii) A method in which isoprene and/or 1,3-butadiene and an aromatic vinyl compound are sequentially polymerized by using a dilithium compound as a polymerization initiator.

Examples of the above-mentioned alkyllithium compound include methyllithium, ethyllithium, n-butyllithium, sec-butyllithium, tert-butyllithium, and pentyllithium. Examples of the coupling agent include dichloromethane, dibromomethane, dichloroethane, dibromoethane, dibromobenzene, and phenyl benzoate. Examples of the dilithium compound include naphthalenedilithium and dilithiohexylbenzene.

The use amount of the polymerization initiator such as the above-mentioned alkyllithium compound and dilithium compound and that of the coupling agent are each determined arbitrarily depending on desired weight average molecular weights of a target styrene-based thermoplastic elastomer (a). Usually, the polymerization initiator such as an alkyllithium compound and a dilithium compound is used at a ratio of 0.01 to 2 parts by mass with respect to 100 parts by mass of the total of polymerizable monomers to be polymerized such as an aromatic vinyl compound, 1,3-butadiene, and isoprene. When a coupling agent is used, it is used at a ratio of 0.001 to 10 parts by mass with respect to 100 parts by mass of the total of the polymerizable monomers.

The above-mentioned anionic polymerization is preferably carried out in the presence of a solvent. Any solvent can be used without particular limitation as long as the solvent is inert to the polymerization initiator and does not adversely affect polymerization reaction. Examples of the solvent include saturated aliphatic hydrocarbons or aromatic hydrocarbons such as hexane, heptane, octane, decane, toluene, benzene, and xylene.

Further, polymerization reaction can be carried out at a temperature of usually 0 to 80° C., preferably 10 to 70° C. and for usually 0.5 to 50 hours, preferably 1 to 30 hours in the case of adopting any of the above-mentioned methods (i) to (iii).

Further, in order to control the content of a 1,2-bond and a 3,4-bond (degree of vinylation) in the polymer block (B) contained in the styrene-based thermoplastic elastomer (a) to 30 to 85 mol % and control the glass transition temperature of the polymer block (B) to −50 to 30° C., it is possible to use a method in which a Lewis base is added as a co-catalyst at the time of the polymerization of the polymer block (B).

Examples of the Lewis base to be used include: ethers such as dimethyl ether, diethyl ether, and tetrahydrofuran; glycol ethers such as ethylene glycol dimethyl ether and diethylene glycol dimethyl ether; and amines such as triethylamine, N,N,N',N'-tetramethylenediamine, and N-methylmorpholine. One kind of those Lewis bases may be used alone, or two or more kinds thereof may be used in combination.

The addition amount of the Lewis base is determined depending on the extent to which the bond amount of the isoprene unit and/or the 1,3-butadiene unit that forms the polymer block (B) is controlled. Thus, the addition amount of the Lewis base is not limited in a strict sense, but the Lewis base is used in the range of usually 0.1 to 1,000 moles, preferably 1 to 100 moles with respect to 1 gram atom of lithium contained in an alkyllithium compound or dilithium compound to be used as a polymerization initiator.

After polymerization is carried out by any of the above-mentioned methods, a block copolymer contained in the resultant polymerization reaction liquid is coagulated by pouring the polymerization reaction liquid in a poor solvent (such as methanol) for the block copolymer, or the resultant polymerization reaction liquid is poured in hot water while being steamed to remove a solvent by azeotropy (steam stripping), followed by drying, thereby being able to yield an unhydrogenated block copolymer.

[Hydrogenation of Block Copolymer]

Subsequently, the block copolymer obtained as described above is subjected to a hydrogenation reaction, thereby being able to produce a hydrogenated block copolymer, that is, a styrene-based thermoplastic elastomer (a).

The hydrogenation reaction can be carried out by dissolving the block copolymer obtained as described above in a solvent which is inert in a reaction system and causing the block copolymer to react with hydrogen, in the presence of a catalyst for hydrogenation such as: Raney nickel; a heterogeneous catalyst in which a metal such as Pt, Pd, Ru, Rh, or Ni is supported by a carrier such as carbon, alumina, or diatom earth; a Ziegler catalyst formed of a combination of a transition metal compound and any of an alkylaluminum compound, an alkyllithium compound, and the like; or a metallocene-based catalyst.

The hydrogenation reaction can be carried out by controlling the hydrogen pressure in the range of usually 0.1 to 20 MPa, preferably 0.5 to 15 MPa, the reaction temperature in the range of usually 20 to 250° C., preferably 50 to 150° C., and the reaction time in the range of usually 0.1 to 100 hours, preferably 1 to 50 hours.

Note that it is also possible to subject the polymerization reaction liquid containing a block copolymer obtained as described above, as it is, to a hydrogenation reaction without isolating the block copolymer from the polymerization reaction liquid. If this method is adopted, a hydrogenated reaction liquid is poured in a poor solvent such as methanol to coagulate a block copolymer, or a hydrogenated reaction liquid is poured in hot water while being steamed to remove a solvent by azeotropy (steam stripping), followed by drying, thereby being able to yield a hydrogenated styrene-based thermoplastic elastomer (a).

The styrene-based thermoplastic elastomer (a) obtained as described above may be used as it is in a grain form or in a powder form. Alternatively, the styrene-based thermoplastic elastomer (a) may be pelletized, if necessary, by using a conventionally well-known method, to thereby produce pellets of the styrene-based thermoplastic elastomer (a).

Examples of a pelletization method include a method involving extruding a styrene-based thermoplastic elastomer (a) so as to have a strand shape from a single or twin screw extruder and cutting the strand in water with a rotating blade provided at the front surface of a die portion, and a method involving extruding a styrene-based thermoplastic elastomer (a) so as to have a strand shape from a single or twin screw extruder, cooling the strand with water or air, and then cutting it with a strand cutter.

<Polypropylene-Based Resin (b)>

The polypropylene-based resin (b) to be used in the present invention may be any polypropylene-based resin such as homopolypropylene, a random polypropylene produced by copolymerization with ethylene or an α-olefin, and a block polypropylene produced by copolymerization with ethylene or an α-olefin blockwise.

Examples of the α-olefin in the copolymer include α-olefins each having 20 or less carbon atoms, such as 1-butene, 1-pentene, 3-methyl-1-butene, 1-hexene, 3-methyl-1-pentene, 4-methyl-1-pentene, 1-heptene, 1-octene, 1-nonene, 1-decene, 1-dodecene, 1-tetradecene, 1-hexadecene, 1-octadecene, and 1-eicosene. One kind of those α-olefins may be used alone, or two or more kinds thereof may be used in combination.

The copolymerization ratio of ethylene in the above-mentioned copolymer is usually 1 to 30 mass %, preferably 5 to 28 mass % in the copolymer, and the copolymerization ratio of the α-olefin is usually 30 mass % or less, preferably 20 mass % or less in the copolymer.

Preferably used as the above-mentioned polypropylene-based resin (b) are a polypropylene homopolymer, a propylene-ethylene random copolymer, a propylene-1-butene random copolymer, a propylene-ethylene-1-butene random copolymer, and a propylene-1-hexene random copolymer. One kind of those polypropylene-based resins (b) may be used alone, or two or more kinds thereof may be used in combination.

The melt flow rate of the polypropylene-based resin (b) is preferably determined from the standpoint that the crystallinity of the polypropylene-based resin (b) is increased by promoting its crystallization, thereby producing a tube having excellent clamp resistance, anti-conglutination property, and kink resistance. From that standpoint, the melt flow rate (MFR) at a temperature of 230° C. and at a load of 21.2 N is preferably 10 to 50 g/10 minutes, more preferably 15 to 50 g/10 minutes, still more preferably 20 to 50 g/10 minutes. Such polypropylene-based resin having high fluidity has not been used in combination with a styrene-based thermoplastic elastomer in the past because of its difficulty in forming a shape and the like.

It is estimated that, if a polypropylene-based resin (b) having an MFR in the above-mentioned range is used, the difference in melt viscosity between the polypropylene-based resin (b) and the styrene-based thermoplastic elastomer (a) becomes larger, and consequently, the compatibility of the both properly lowers and their phase separation is promoted, resulting in the promotion of the fine crystallization of the polypropylene-based resin (b). As a result, the ratio of fine crystals produced in a tube becomes higher, leading to the increase of the ratio of diffraction peak intensities [I(14)/I(15)], thereby yielding a tube having excellent clamp resistance, anti-conglutination property, and kink resistance.

Note that the melt flow rate (MFR) can be determined in accordance with JIS K7210.

Further, as the polypropylene-based resin (b) has a higher crystallinity and has a higher crystallization temperature in a resin composition to be used in the present invention, that is, as the polypropylene-based resin (b) has a higher crystallization speed, there is provided a tube having a higher ratio of fine crystals produced in a tube. In order to control appropriately the crystallinity in the resultant tube, it is possible to add an additive such as a nucleating agent or a lubricant or change the copolymerization components or copolymerization ratio of the polypropylene-based resin (b).

It is critical for the resin composition to be used in the present invention not to include a softening agent. Known as the softening agent are, for example, a paraffin-based process oil, a naphthene-based process oil, a liquid paraffin, and a low-molecular-weight polyethylene, and some of them are used for imparting flexibility and kink resistance. However, if any of these softening agents is added, the surface of the tube produced from the resultant resin composition exhibits high tackiness, and its clamp resistance lowers. Further, tubes are conglutinated to each other at the time of their sterilization or storage, with the result that handling tubes becomes difficult, which fact is not preferred. Further, there is a possibility of causing a serious problem such as the problem that the softening agent is eluted from the surface of a tube into a content liquid passing through the inside of the tube, thereby being injected into blood.

<Resin Composition Containing (a) and (b) Components>

The blending ratio of the styrene-based thermoplastic elastomer (a) and the polypropylene-based resin (b) in the resin composition to be used in the present invention is such that, when the styrene-based thermoplastic elastomer (a) is referred to as a component (a) and the polypropylene-based resin (b) is referred to as a component (b), the mass ratio of the component (a) to the component (b), [(a)/(b)], should be 90/10 to 40/60, preferably 80/20 to 45/55, more preferably 70/30 to 50/50.

When the ratio of the styrene-based thermoplastic elastomer (a) in the resin composition is more than 90 mass %, or when the ratio of the polypropylene-based resin (b) is less than 10 mass %, fine crystals are difficult to be produced in the resultant tube of the present invention, and the tube produced from the resin composition may have insufficient clamp resistance and anti-conglutination property. On the other hand, when the ratio of the styrene-based thermoplastic elastomer (a) in the resin composition is less than 40 mass %, or when the ratio of the polypropylene-based resin (b) is more than 60 mass %, the crystallinity of the resultant resin composition becomes too high, with the result that the flexibility of the tube produced from the resin composition remarkably lowers, sometimes leading to the reduction of its kink resistance, and hence the above-mentioned ratios are not preferred.

The resin composition to be used in the present invention may contain any other polymer as long as the object of the present invention is not impaired. Examples of the other polymer include polyisoprene, polybutadiene, a styrene-butadiene rubber, a styrene-isoprene rubber, polyethylene, an ethylene-vinyl acetate copolymer, an ethylene-ethyl acrylate copolymer, an ethylene-(meth) acrylic acid copolymer, a metal ion cross-linked resin of the ethylene-(meth)acrylic acid copolymer (ionomer), styrene-based resins such as polystyrene, an AS resin, and an ABS resin, polyphenylene ether-based resins, polyamide-based resins such as nylon 6 and nylon 66, polyester-based resins such as polyethylene terephthalate and polybutylene terephthalate, a polyurethane-based resin, acetal-based resins such as a polyoxymethylene homopolymer and a polyoxymethylene copolymer, acrylic resins such as a polymethyl methacrylate-based resin, a block, random, or tapered copolymer or copolymer having a partial block structure formed of an aromatic vinyl compound and isoprene and/or 1,3-butadiene, and hydrogenated products thereof.

The blending amount of the above-mentioned other polymer is, if it is added, preferably 100 parts by mass or less with respect to 100 parts by mass of the above-mentioned resin composition, more preferably 60 parts by mass or less, from the standpoint of imparting good kink resistance and anti-conglutination property to the tube produced from the resultant resin composition.

It is possible for the resin composition to be used in the present invention to include additionally a hydrogenated block copolymer prepared by hydrogenating a block copolymer formed of a polymer block (C) mainly containing an aromatic vinyl compound and a polymer block (D) mainly containing isoprene and/or 1,3-butadiene. In this case, the glass transition temperature of the polymer block (D) in the copolymer to be added is preferably −45° C. or more. It is not preferred that the glass transition temperature be less than −45° C., because the tube produced from the resultant resin composition have insufficient transparency and flexibility.

The resin composition to be used in the present invention may have added thereto a tackifying resin, an inorganic filler, or a lubricant as long as the object of the present invention is not impaired.

Examples of the tackifying resin include a rosin-based resin, a terpene phenol resin, a terpene resin, an aromatic hydrocarbon-modified terpene resin, an aliphatic petroleum resin, an alicyclic petroleum resin, an aromatic petroleum resin, a coumarone-indene resin, a phenolic resin, and a xylene resin.

When the tackifying resin is added, its blending amount is preferably 50 parts by mass or less, more preferably 30 parts by mass or less with respect to 100 parts by mass of the above-mentioned resin composition from the viewpoints of the kink resistance and anti-conglutination property of the tube formed of the resultant resin composition.

Examples of the inorganic filler include talc, clay, mica, calcium silicate, calcium carbonate, magnesium carbonate, aluminum hydroxide, magnesium hydroxide, calcium hydroxide, silica, alumina, titanium oxide, iron oxide, zinc oxide, and magnesium oxide. The resin composition to be used in the present invention preferably does not contain the inorganic filler from the viewpoint of transparency. However, when the inorganic filler is added from the viewpoint of an improvement in desired performance, its blending amount is preferably 3 parts by mass or less, more preferably 2 parts by mass or less with respect to 100 parts by mass of the above-mentioned resin composition from the viewpoint of transparency of the tube formed of the resultant resin composition.

Examples of the lubricant include: fatty acids such as stearic acid; fatty acid amides such as stearic acid amide, oleic amide, erucamide, behenamide, and ethylenebisstearic acid amide; fatty acid esters such as stearic acid monoglyceride and butyl stearate; and metal soaps such as calcium stearate and calcium oleate. The blending amount of the lubricant is, if it is added, preferably in the range of 0.01 to 1 part by mass with respect to 100 parts by mass of the above-mentioned resin composition, more preferably in the range of 0.05 to 0.5 part by mass, still more preferably in the range of 0.05 to 0.2 part by mass, from the standpoint of imparting good transparency, kink resistance, clamp resistance, and anti-conglutination property to the tube produced from the resin composition.

Besides, it may be possible to add, if necessary, additionally to the resin composition to be used in the present invention, other additives such as a processing heat stabilizer, a photo-stabilizer, an ultraviolet absorber, an antioxidant, a colorant, an antistatic agent, a flame retardant, a water repellent, a water-proofing agent, a hydrophilicity-imparting agent, an electrical conductivity-imparting agent, a heat conductivity-imparting agent, an electromagnetic wave shielding property-imparting agent, a translucency adjuster, a fluorescent agent, a sliding property-imparting agent, a transparency-imparting agent, an anti-blocking agent, a metal deactivator, and an antibacterial agent, in the range of the content at which each additive does not impair the object of the present invention. Examples of the processing heat stabilizer include a phosphorus-based processing heat stabilizer, a lactone-based processing heat stabilizer, and a hydroxyl-based processing heat stabilizer. Of those, a lactone-based processing heat stabilizer is preferred, and the content thereof is preferably 3 parts by mass or less with respect to 100 parts by mass of the above-mentioned resin composition, preferably 2 parts by mass or less, from the standpoint of imparting good transparency to the tube produced from the resin composition.

The resin composition to be used in the present invention can be produced by mixing the styrene-based thermoplastic elastomer (a), the propylene-based resin (b), and other components added if necessary by using a mixing machine such as a Henschel mixer, a V blender, a ribbon blender, a tumbler blender, or a conical blender, or can be produced by melt-kneading, after the mixing, the mixture by using a single screw or twin screw extruder, a kneader, or the like.

The resultant resin composition is preferably pelletized in order to be easily formed into a tube. The melting temperature at the time of kneading can be arbitrarily set, but it is usually 150 to 300° C., preferably 160 to 250° C.

<Tube>

The tube of the present invention can be produced by forming a resin composition into a tube having a desired shape, which includes the styrene-based thermoplastic elastomer (a) and the polypropylene-based resin (b). In this case, the ratio of a diffraction peak intensity [I(14)] at a scattering angle (2θ) of 14° to a diffraction peak intensity [I(15)] at a scattering angle (2θ) of 15°, that is, [I(14)/I(15)], in a wide-angle X-ray diffraction pattern of the resultant tube measured from its side surface direction, should be 1.4 or more, and is preferably 1.5 or more, more preferably 1.7 or more. It is not preferred that the above-mentioned ratio of the diffraction peak intensities be less than 1.4, because the clamp resistance and the anti-conglutination property lower. On the other hand, it is not preferred that the ratio of the diffraction peak intensities be more than 4, because the flexibility, the transparency, and the kink resistance lower in some cases.

The wide-angle X-ray diffraction profile of a tube can be obtained by cutting the tube open in the longitudinal direction, thereby producing a reed-shaped sheet, and causing X-rays to be incident into the sheet. In this case, as shown in FIG. 1, sharp diffraction peaks are detected relatively strongly, while overlapping with a broad amorphous peak, mainly at scattering angles (2θ) of 14.0°, 16.8°, 18.5°, 21.0°, and 21.8°. These are diffraction peaks derived from α-type crystals of polypropylene, and these peaks are attributed to the diffractions caused by the (110), (040), (130), (111), and (13-1)+(041) surfaces, respectively. These peaks do not have anisotropy in the azimuth direction, and hence it is found from the fact that no orientation is present in the tube and isotropic crystals of polypropylene are produced.

Thus, the above-mentioned ratio of the diffraction peak intensities corresponds to the content ratio of the crystals of the polypropylene-based resin (b) with respect to the whole tube. Actually, the crystallinity calculated on the basis of a curve fitting method was found to have a high correlation with the above-mentioned ratio of the diffraction peak intensities. However, when a curve fitting method is adopted, different values may be obtained depending on its analytical methods, and hence evaluation was performed in the present invention by using the ratio of diffraction peak intensities, which is highly reproducible.

It is not clear why the tube of the present invention has excellent clamp resistance, anti-conglutination property, and kink resistance, but it is estimated that there is proper compatibility between the styrene-based thermoplastic elastomer (a) and the polypropylene-based resin (b), thus forming extremely fine, non-anisotropic crystals of the polypropylene-based resin at a proper crystallization speed, and consequently, the whole tube has fine crystals in a larger amount.

In order to obtain proper compatibility between the styrene-based thermoplastic elastomer (a) and the polypropylene-based resin (b), it is necessary to control the hydrogenation ratio of the polymer block (B) in the styrene-based thermoplastic elastomer (a) to 70% or more and control the content of the 1,2-bond and the 3,4-bond to 30 to 85 mol %. Moreover, it is necessary to produce crystals of the polypropylene-based resin in a tube so that the ratio of X-ray diffraction intensities of the tube, [I(14)/I(15)], becomes 1.4 or more.

The tube produced from the above-mentioned resin composition has a crystallization temperature of preferably 95° C. or more, more preferably 97° C. or more, still more preferably 100° C. or more, the crystallization temperature being measured with a differential scanning calorimeter (DSC) under the condition of a cooling speed of 10° C./minute. In the DSC measurement, the crystallization temperature of the tube observed at the time of cooling corresponds to the crystallization speed of the polypropylene-based resin, and hence, as the crystallization temperature is higher, the crystallization speed is faster. Thus, the crystallization speed is adjusted in the range of not being too fast, thereby yielding a tube having excellent clamp resistance, anti-conglutination property, and kink resistance.

[Production of Tube]

There is no particular limitation on a method of producing the tube of the present invention. For example, there is given a method involving feeding a resin composition obtained as described above in an extruder, melting the resin composition, and forming the molten composition into a product having a tube shape through a die, followed by water cooling or air cooling, thereby yielding a tube. A single screw or multi-screw extruder can be used as the extruder used in the method. Further, it is also possible to form a resin composition into a tube directly with an extruder at the time of producing the resin composition.

There is no particular limitation on the shape of the cross-section of the tube of the present invention produced by using such method as described above, but the tube generally preferably has a circular shape, an elliptical shape, or the like in its cross-section. There is no particular limitation on the size of the tube. For example, the outer diameter of the tube is preferably 1 to 50 mm, more preferably 2 to 30 mm, still more preferably 3 to 20 mm. The thickness of the tube is preferably 0.3 to 30 mm, more preferably 0.4 to 20 mm, still more preferably 0.5 to 10 mm.

Further, when the cooling speed of a tube is slow at the time of its formation, the tube has high crystallinity, and hence, in order to control the crystallinity of the resultant tube appropriately, it is possible to adjust the cooling speed of a tube appropriately at the time of its formation.

The tube of the present invention can be a multilayered tube produced by additionally laminating any other polymer by a multilayer extrusion method as long as the object of the present invention is not impaired.

Examples of the polymer to be laminated include: olefin-based polymers such as polypropylene, polyethylene, an ethylene-propylene copolymer rubber (EPM), and an ethylene-propylene-nonconjugated diene copolymer rubber (EPDM); polyester-based polymers such as a polyester elastomer, polyethylene terephthalate, and polybutylene terephthalate; polyamide-based resins such as polyamide 6, polyamide 6/6, polyamide 6/10, polyamide 11, polyamide 12, and polyamide 6/12; acrylic resins such as polymethyl acrylate and polymethyl methacrylate; polyoxymethylene-based resins such as a polyoxymethylene homopolymer and a polyoxymethylene copolymer; styrene-based resins such as a styrene homopolymer, an acrylonitrile-styrene resin, and an acrylonitrile-butadiene-styrene resin; a polycarbonate resin; styrene-based elastomers such as a styrene-butadiene copolymer rubber and a styrene-isoprene copolymer rubber, and hydrogenated products or modified products thereof; a natural rubber; a synthetic isoprene rubber and a liquid polyisoprene rubber, and hydrogenated products or modified products thereof; a chloroprene rubber; an acrylic rubber; a butyl rubber; an acrylonitrile-butadiene rubber; an epichlorohydrin rubber; a silicone rubber; a fluororubber; chlorosulfonated polyethylene; a urethane rubber; a polyurethane-based elastomer; a polyamide-based elastomer; a polyester-based elastomer; and a soft vinyl chloride resin.

These polymers can be used in any of the innermost layer, middle layer, and outermost layer of a multilayered tube depending on the performances desired to be imparted to the multilayered tube. Further, the multilayered structure may be applied to part of a tube, may be a multilayered structure having an intermittent multilayer, or may be a multilayered structure including sites made of different kinds of materials.

Further, in the present invention, in order to improve the pressure resistance and the like of a tube while suppressing the increase of its thickness and maintaining its flexibility, a knitted or braided reinforcing thread or a spiral reinforcing body can be wound around the tube to make a pressure-resistant tube (hose). The knitted or braided reinforcing thread is placed at the inner portion or between layers in the thickness direction, and it is possible to use a vinylon fiber, a polyamide fiber, a polyester fiber, an aramid fiber, a carbon fiber, a metal wire, or the like to produce the knitted or braided reinforcing thread. The spiral reinforcing body is placed at the outer circumference, and a metal, a plastic, or the like can be used to produce it.

<Medical Device>

A medical device of the present invention is characterized by using the tube of the present invention.

Examples of the medical device include medical devices used at the time of infusion, blood transfusion, peritoneal dialysis, catheter treatment, and the like, such as catheters (an implantable catheter, a balloon catheter, and the like), a tube for an infusion bag, a tube for a blood bag, a blood vessel prosthesis, a blood circuit, a syringe, a hemodialyzer, a blood component separator, and an oxygenator.

Note that, in any of these medical devices, the whole part is not necessary to be formed of the resin composition described above, and it is acceptable that at least parts contacting a body fluid are formed of the resin composition described above. For example, in any of the above-mentioned catheters, blood bag, and other devices, it may be possible that parts contacting a body fluid are formed of the resin composition described above and other parts not contacting the body fluid are formed of other resins used for medical application, such as soft vinyl chloride resin and polyurethane.

EXAMPLES

Hereinafter, the present invention is described in more detail with reference to examples, but the present invention is by no means limited to the examples. Note that in the examples and comparative examples, test pieces were produced and each physical property was measured or evaluated according to the manners described below.

(1) Content of Styrene and Content of 1,2-Bond and 3,4-Bond

A styrene-based thermoplastic elastomer was dissolved in a deuterated chloroform solvent and "Lambda-500" manufactured by JEOL Ltd. was used to measure $^1$H-NMR spectra at 50° C. The resultant spectra were used to calculate the content of styrene and the content of a 1,2-bond and a 3,4-bond.

(2) Hydrogenation Ratio

The iodine values of a styrene-based thermoplastic elastomer before and after hydrogenation reaction were measured, and the ratio of the values was used to calculate the hydrogenation ratio of the styrene-based thermoplastic elastomer.

(3) Glass Transition Temperature

A differential scanning calorimeter "DSC200" manufactured by Seiko Instruments Inc. was used to read the temperature of the inflection point in a measurement curve prepared on the basis of a rate of temperature increase of 10° C./minute. The temperature was determined as the glass transition temperature of a styrene-based thermoplastic elastomer.

(4) Crystallization Temperature

A differential scanning calorimeter "DSC200" manufactured by Seiko Instruments Inc. was used to read the temperature of the exothermic peak top, which was measured when the temperature of a test piece was increased from room temperature to 180° C. at a rate of 10° C./minute, was kept at 200° C. for 10 minutes, and was lowered to room temperature at a rate of 10° C./minute, and the temperature of the exothermic peak top was determined as the crystallization temperatures of a polypropylene-based resin and a tube.

(5) Melt Flow Rate (MFR)

MFR was measured under the conditions of a temperature of 230° C. and a load of 21.2 N in accordance with JIS K7210.

(6) Wide-Angle X-Ray Diffraction

A tube (4.0 mm in outer diameter, 3.0 mm in inner diameter, and 0.5 mm in thickness) produced in each of the examples and the comparative examples was cut open in the longitudinal direction, thereby producing a reed-shaped sheet (0.5 mm in thickness), which was used as a measurement sample. The resultant sample was used to measure an X-ray diffraction pattern by using "D8 DISCOVER with GADDS" (X-ray source: Cu$\kappa\alpha$ radiation, $\lambda$=0.15418 nm, detector: HISTER two-dimensional PSPC) manufactured by Bruker AXS K.K. The sample was placed so that the length direction of the original tube was perpendicular to the rotating surface of a goniometer and the surface of the sample was slanted by 11° with respect to incident X-rays. For the incident X-rays, a tube voltage and a tube current were set to 45 kV and 110 mA, respectively, and a collimator having a diameter of 0.5 mm was used. The detector was installed at the position of a scattering angle (2θ) of 22° and a camera length of 15.0 cm. Each sample was subjected to integrated measurement for 300 seconds, yielding a scattering pattern.

An X-ray diffraction intensity curve with respect to a scattering angle 2θ was derived from the resultant scattering pattern, by using software "Bruker Analytical X-ray Systems GADDS for NWT 4.1.23" manufactured by Bruker AXS K.K. in a 2θ range of 5 to 40°, in a χ range of −150° to −30°, at an interval of 0.01°, and using "5-Bin normalized" as a method for intensity normalization. In the X-ray diffraction intensity curve, when the straight line connecting the diffraction intensity [I'(5)] at 2θ=5° with the diffraction intensity [I'(30)] at 2θ=30° was defined as a base line, the intensity of the diffraction peak top (diffraction caused by the (110) surface of an crystal of a polypropylene resin) existing at 2θ=14° from the base line was represented by I(14) and the diffraction intensity at 2θ=15° from the base line was represented by I(15). Then, the ratio of the intensities, I(14)/I(15), was calculated. Moreover, the X-ray diffraction curve of a tube from which the base line was subtracted was used to calculate the crystallinity of a polypropylene resin based on the whole tube by using the following curve fitting methods (i) to (iii).

(i) A peak symmetric with respect to the central line at 2θ=17.5° is set as an amorphous peak, the height at 2θ=17.5° is determined in conformity to an actually measured curve, and fitting is performed by using a shape constant (Gaussian type/Lorentzian type), a full-width at half maximum, and the degree of asymmetry as variable parameters.

(ii) Next, a bilaterally symmetric peak is set as an amorphous peak at each of the positions of scattering angles (2θ) of 14°, 16.5°, 18.5°, and 21°, and fitting of only the crystal peak is performed by using a height, a shape constant, and a full-width at half maximum as variable parameters.

(iii) The resultant area of the amorphous peak (Aa) and the resultant area of the crystal peak (Ac) are used to calculate the crystallinity=Ac/(Aa+Ac).

(7) Transparency

Five tubes (4.0 mm in outer diameter, 3.0 mm in inner diameter, and 0.5 mm in thickness) produced in each of the examples and the comparative examples were arranged in line, and a haze meter ("HR-100" manufactured by Murakami Color Research Laboratory Co., Ltd.) was used to measure the transmittance (%) of the tubes by using incident light from a side of each tube in accordance with ASTM D-1003.

(8) Flexibility of Tube

A tube (4.0 mm in outer diameter, 3.0 mm in inner diameter, and 0.5 mm in thickness) produced in each of the examples and the comparative examples was used to measure its Young's modulus at the time of stretching the tube at a stretching rate of 5 mm/minute by using a tensile testing machine ("5566" manufactured by Instron Corporation). The Young's modulus was used as the indicator of the flexibility of the tube.

(9) Kink Resistance

A tube having a full length of 20 cm (4.0 mm in outer diameter, 3.0 mm in inner diameter, and 0.5 mm in thickness) produced in each of the examples and the comparative examples was used to measure the circumferential length (mm) of the minimum bending of the tube immediately before its kink when the tube was deformed at 25° C. so as to have a circular shape, and the resultant value was used as the indicator of the kink resistance of the tube. The circumferential length (mm) of the tube immediately before its kink was converted to the corresponding diameter, which was used as the value indicating the kink resistance.

(10) Clamp Resistance

The inside of a tube having a full length of 200 mm (4.0 mm in outer diameter, 3.0 mm in inner diameter, and 0.5 mm in thickness) produced in each of the examples and the comparative examples was filled with a physiological saline. The tube was placed vertically and a medical tube clamp was used to clamp the tube so as to prevent the physiological saline from leaking for 22 hours at the position of 10 mm from the lower end of the tube. After that, the clamp was removed, followed by the measurement of the time (second) taken until all the amount of the physiological saline in the tube completely flowed out from the bottom portion of the tube. The time was used as the indicator of the clamp resistance of the tube.

(11) Anti-Conglutination Property

Two tubes each having a full length of 20 cm (4.0 mm in outer diameter, 3.0 mm in inner diameter, and 0.5 mm in thickness) produced in each of the examples and the comparative examples were stacked and fixed with tape. Then, the tubes were placed in a hot air dryer at 100° C., taken out 30 minutes later, and cooled at room temperature. After that, the conglutination property between the tubes was examined.

A case where no conglutination was found was represented by Symbol ○, and a case where even slight conglutination was found was represented by Symbol x.

(12) Solvent Adhesion

A tube having a full length of 70 mm (4.0 mm in outer diameter, 3.0 mm in inner diameter, and 0.5 mm in thickness) produced in each of the examples and the comparative examples was put in cyclohexane until a portion about 10 mm from one end was immersed therein. Then, a tube-like part (4.0 mm in diameter) of a connector made of polypropylene was fit by 5 mm at the inside of the one end of the tube to cause adhesion of their contact portions. After 24 hours passed, measurement was performed on the tensile strength upon tearing off of the tube and the connector from each other by 300 mm/minute, and the tensile strength was used as the indicator of the solvent adhesion.

Production Example 1

Production of Styrene-Based Thermoplastic Elastomer (a-1)

There were fed, into a pressure-resistant container in which nitrogen substitution and drying had been performed, 80 L of cyclohexane as a solvent, 0.12 L of sec-butyllithium as an initiator, and 0.3 L of tetrahydrofuran as a Lewis base. After the temperature in the container was raised to 50° C., 0.39 L of styrene was added to perform polymerization for 3 hours. Subsequently, a mixed liquid of 6.8 L of isoprene and 7.5 L of 1,3-butadiene was added, followed by polymerization for 4 hours, and then, 1.18 L of styrene were further added, followed by polymerization for 3 hours. The resultant polymerization reaction liquid was poured into 80 L of methanol, and the precipitated solid was separated by filtration, followed by drying at 50° C. for 20 hours, thereby yielding a polystyrene-poly(isoprene/butadiene)-polystyrene triblock copolymer in which the content of a 1,2-bond and a 3,4-bond was 65 mol %.

Next, 10 kg of the resultant polystyrene-poly(isoprene/butadiene)-polystyrene triblock copolymer were dissolved in 200 L of cyclohexane, and palladium carbon (content of palladium supported: 5 mass %) was added as a hydrogenation catalyst at 5 mass % with respect to the copolymer. Then, the mixture was subjected to a reaction for 10 hours under the conditions of a hydrogen pressure of 2 MPa and a temperature of 150° C. After cooling and pressure discharge, the palladium carbon was removed by filtration and the filtrate was then concentrated, followed by vacuum drying, thereby yielding a hydrogenated polystyrene-poly(isoprene/butadiene)-polystyrene triblock copolymer.

It was found that the [Mw(A1)/Mw(A2)] of the resultant polymer was 0.30, the glass transition temperature was −30° C., the content of styrene was 12 mass %, the hydrogenation ratio was 85%, and the weight average molecular weight was 130,000.

Production Example 2

Production of Styrene-Based Thermoplastic Elastomer (a-2)

A polymerization reaction and a hydrogenation reaction were performed in the same manner as that used for producing the styrene-based thermoplastic elastomer (a-1), except that 0.07 L of sec-butyllithium as an initiator and 0.3 L of tetrahydrofuran as a Lewis base were fed, and 0.39 L of styrene, a mixed liquid of 6.8 L of isoprene and 7.5 L of 1,3-butadiene, and 0.39 L of styrene were sequentially added as monomers for polymerization to perform polymerization, there by yielding 10 kg of a hydrogenated polystyrene-poly(isoprene/butadiene)-polystyrene triblock copolymer in which the content of a 1,2-bond and a 3,4-bond was 65 mol %.

It was found that the [Mw(A1)/Mw(A2)] of the resultant polymer was 1.00, the glass transition temperature was −30° C., the content of styrene was 7 mass %, the hydrogenation ratio was 90%, and the weight average molecular weight was 210,000.

Production Example 3

Production of Styrene-Based Thermoplastic Elastomer (a-3)

A polymerization reaction and a hydrogenation reaction were performed in the same manner as that used for producing the styrene-based thermoplastic elastomer (a-1), except that 0.09 L of sec-butyllithium as an initiator and 0.3 L of tetrahydrofuran as a Lewis base were fed, and 0.44 L of styrene, a mixed liquid of 6.7 L of isoprene and 7.4 L of 1,3-butadiene, and 0.44 L of styrene were sequentially added as monomers for polymerization to perform polymerization, there by yielding 10 kg of a hydrogenated polystyrene-poly(isoprene/butadiene)-polystyrene triblock copolymer in which the content of a 1,2-bond and a 3,4-bond was 65 mol %.

It was found that the [Mw(A1)/Mw(A2)] of the resultant polymer was 1.00, the glass transition temperature was −32° C., the content of styrene was 8 mass %, the hydrogenation ratio was 88%, and the weight average molecular weight was 160,000.

Production Example 4

Production of Styrene-Based Thermoplastic Elastomer (a-4)

A polymerization reaction and a hydrogenation reaction were performed in the same manner as that used for producing the styrene-based thermoplastic elastomer (a-1), except that 0.13 L of sec-butyllithium as an initiator and 0.2 L of tetrahydrofuran as a Lewis base were fed, and 1.60 L of styrene, 16.0 L of isoprene, and 1.60 L of styrene were sequentially added as monomers for polymerization to perform polymerization, thereby yielding 13 kg of a hydrogenated polystyrene-polyisoprene-polystyrene triblock copolymer in which the content of a 1,2-bond and a 3,4-bond was 75 mol %.

It was found that the [Mw(A1)/Mw(A2)] of the resultant polymer was 1.00, the glass transition temperature was −15° C., the content of styrene was 20 mass %, the hydrogenation ratio was 84%, and the weight average molecular weight was 120,000.

Production Example 5

Production of Styrene-Based Thermoplastic Elastomer (a-5)

A polymerization reaction and a hydrogenation reaction were performed in the same manner as that used for producing the styrene-based thermoplastic elastomer (a-1), except that 0.18 L of sec-butyllithium as an initiator and 0.10 L of N,N,N',N'-tetramethylenediamine as a Lewis base were fed, and 0.90 L of styrene, 16.6 L of 1,3-butadiene, and 0.90 L of styrene were sequentially added as monomers for polymerization to perform polymerization, thereby yielding 11 kg of a hydrogenated polystyrene-polybutadiene-polystyrene triblock copolymer in which the content of a 1,2-bond was 77 mol %.

It was found that the [Mw(A1)/Mw(A2)] of the resultant polymer was 1.00, the glass transition temperature was −45° C., the content of styrene was 13 mass %, the hydrogenation ratio was 99%, and the weight average molecular weight was 190,000.

Production Example 6

Production of Hydrogenated Block Copolymer

A polymerization reaction and a hydrogenation reaction were performed in the same manner as that used for producing the styrene-based thermoplastic elastomer (a-1), except that 0.18 L of sec-butyllithium as an initiator and 2.20 L of styrene, a mixed liquid of 6.6 L of isoprene and 7.5 L of 1,3-butadiene, and 2.20 L of styrene as monomers for polymerization were sequentially added to perform polymerization, thereby yielding 13 kg of a hydrogenated polystyrene-poly(isoprene/butadiene)-polystyrene triblock copolymer in which the content of a 1,2-bond and a 3,4-bond was 5 mol %.

It was found that the [Mw(A1)/Mw(A2)] of the resultant polymer was 1.00, the glass transition temperature was −55° C., the content of styrene was 30 mass %, the hydrogenation ratio was 98%, and the weight average molecular weight was 100,000.

[Details of Polypropylene-Based Resins]

b-1: random polypropylene "PURELL RP373R" (MFR=25.0 g/10 minutes (230° C., 21.2 N)) manufactured by LyondellBasell Industries b-2: random polypropylene "PURELL RP378T" (MFR=48.0 g/10 minutes (230° C., 21.2 N)) manufactured by LyondellBasell Industries b-3: random polypropylene "F327" (MFR=7 g/10 minutes (230° C., 21.2N), melting point: 145° C.) manufactured by Prime Polymer Co., Ltd.

b-4: random polypropylene "J226E" (MFR=30 g/10 minutes (230° C., 21.2 N), melting point: 150° C.) manufactured by Prime Polymer Co., Ltd.

b-5: random polypropylene "COSMPLENE S331" (MFR=3 g/10 minutes (230° C., 21.2 N), melting point: 150° C.) manufactured by The Polyolefin Company

[Other Additives]

Softening agent: paraffin-based process oil "Diana Process Oil PW-90" (manufactured by Idemitsu Kosan Co., Ltd., kinetic viscosity (40° C.): 95.54 mm$^2$/s)

Lubricant: erucamide "Fatty Acid Amide E" (manufactured by Kao Corporation)

Examples 1 to 11, Comparative Examples 1 to 12, and Reference Examples 1 to 3

Any of the styrene-based thermoplastic elastomers (a-1, a-2, a-3, a-4, and a-5) and the hydrogenated block copolymer, which were produced as described above, any of the polypropylene-based resins (b-1, b-2, b-3, b-4, and b-5), the softening agent, and the lubricant were blended at each ratio shown in Tables 1 and 2, and the whole was subjected to melt-kneading at 230° C. with a twin screw extruder, yielding pellets of a resin composition. The resultant pellets were formed into a product having a tube shape by using a single screw extruder equipped with a tube die under a forming condition A (extrusion temperature: 185° C., take-up speed: 10 m/minute), a forming condition B (extrusion temperature: 175° C., take-up speed: 10 m/minute), or a forming condition C (extrusion temperature: 175° C., take-up speed: 20 m/minute), followed by cooling with water in a cooling bath, thereby yielding a tube measuring 4.0 mm in outer diameter, 3.0 mm in inner diameter, and 0.5 mm in thickness.

Each of some resultant tubes was evaluated for its crystallinity, crystallization temperature, transparency, flexibility, kink resistance, clamp resistance, anti-conglutination property, and solvent adhesion, and the results are shown in Tables 1 and 2. Further, each of the tubes produced by being extruded under the forming condition C was evaluated for its transparency, flexibility, kink resistance, clamp resistance, anti-conglutination property, and solvent adhesion, and the results are shown in Table 3. FIG. 1 shows the wide-angle X-ray diffraction patterns of the tubes produced in Examples 1, 2, 4, 7, and 8, Comparative Examples 1, 2, 9, and 10, and Reference Example 1.

TABLE 1

| | | Example | | | | | | | | |
|---|---|---|---|---|---|---|---|---|---|---|
| | | 1 | 2 | 3 | 4 | 5 | 6 | 7 | 8 | 9 |
| Resin composition/ | Thermoplastic elastomer (a) | | | | | | | | | |
| part(s) by mass | a-1 | 60 | 60 | 60 | 60 | 50 | | | | |
| | a-2 | | | | | | | | 60 | 60 |
| | a-3 | | | | | | | | 60 | |
| | a-5 | | | | | | 60 | | | |
| | Hydrogenated block copolymer*1 | | | | | | | | | |
| | Polypropylene-based resin (b) | | | | | | | | | |
| | b-1 (MFR = 25 g/10 minutes) | 40 | | 40 | | 40 | | 40 | 40 | |
| | b-2 (MFR = 48 g/10 minutes) | | 40 | | | | | | | |

TABLE 1-continued

|  |  | Example |  |  |  |  |  |  |  |  |
|---|---|---|---|---|---|---|---|---|---|---|
|  |  | 1 | 2 | 3 | 4 | 5 | 6 | 7 | 8 | 9 |
|  | b-3 (MFR = 7 g/10 minutes) |  |  |  |  |  | 50 |  | 40 |  |
|  | b-4 (MFR = 30 g/10 minutes) |  |  |  | 40 |  |  |  |  |  |
|  | Lubricant |  |  |  |  |  |  |  |  |  |
|  | Erucamide |  |  |  |  |  |  |  |  | 0.1 |
|  | Forming condition | A | A | B | A | A | A | B | B | B |
| Physical properties | I(14)/I(15) | 2.18 | 2.42 | 2.38 | 2.25 | 2.58 | 1.65 | 2.59 | 1.99 | 1.60 |
|  | Crystallinity | 16.9 | 17.7 | 18.1 | 22.4 | 19.1 | 14.1 | 27.0 | 18.9 | 14.0 |
|  | Crystallization temperature (° C.) | 101.5 | 102.6 | 101.1 | 98.3 | 97.6 | 93.8 | 105.5 | 110.9 | 90.1 |
|  | Transparency (%) | 88 | 91 | 87 | 89 | 86 | 81 | 86 | 90 | 88 |
|  | Flexibility (modulus: MPa) | 20.8 | 17.5 | 21.5 | 22.8 | 22.5 | 36.4 | 14.8 | 17.3 | 16.0 |
|  | Kink resistance (mm) | 22 | 19 | 24 | 20 | 23 | 25 | 18 | 16 | 17 |
|  | Clamp resistance (second(s)) | 3 | 4 | 3 | 1 | 1 | 40 | 1 | 1 | 1 |
|  | Anti-conglutination property | ○ | ○ | ○ | ○ | ○ | ○ | ○ | ○ | ○ |
|  | Solvent adhesion (N) | 32 | 25 | 33 | 40 | 36 | 21 | 37 | 45 | 38 |

*1: Hydrogenated styrene-based thermoplastic elastomer having a lower degree of vinylation

TABLE 2

|  |  | Comparative Example |  |  |  |  |  |  |  |  |  | Reference |
|---|---|---|---|---|---|---|---|---|---|---|---|---|
|  |  | 1 | 2 | 3 | 4 | 5 | 6 | 7 | 8 | 9 | 10 | Example 1 |
| Resin composition/ part(s) by mass | Thermoplastic elastomer (a) |  |  |  |  |  |  |  |  |  |  |  |
|  | a-1 | 60 |  | 60 |  | 60 | 85 | 30 |  | 60 | 60 | 40 |
|  | a-4 |  | 60 |  |  |  |  |  |  |  |  |  |
|  | a-5 |  |  |  | 60 |  |  |  |  |  |  |  |
|  | Hydrogenated block copolymer*1 |  |  |  |  |  |  |  | 60 |  |  | 20 |
|  | Polypropylene-based resin (b) |  |  |  |  |  |  |  |  |  |  |  |
|  | b-1 (MFR = 25 g/10 minutes) |  |  |  |  |  | 15 | 70 | 40 |  |  | 40 |
|  | b-3 (MFR = 7 g/10 minutes) | 40 | 40 | 40 | 40 |  |  |  |  |  |  |  |
|  | b-4 (MFR = 30 g/10 minutes) |  |  |  |  |  |  |  |  | 13 | 13 |  |
|  | b-5 (MFR = 3 g/10 minutes) |  |  |  |  | 40 |  |  |  |  |  |  |
|  | Softening agent |  |  |  |  |  |  |  |  |  |  |  |
|  | Paraffin-based process oil |  |  |  |  |  |  |  |  | 27 | 25 |  |
|  | Lubricant |  |  |  |  |  |  |  |  |  |  |  |
|  | Erucamide |  |  |  |  |  |  |  |  |  | 1 |  |
|  | Forming condition | A | A | B | A | A | A | A | A | A | A | A |
| Physical properties | I(14)/I(15) | 1.14 | 1.37 | 1.19 | 1.31 | 1.05 | 1.02 | 4.82 | 4.05 | 0.97 | 1.38 | 1.78 |
|  | Crystallinity | 12.2 | 8.7 | 9.3 | 10.4 | 9.0 | 3.8 | 31.2 | 26.8 | 5.1 | 10.7 | 21.4 |
|  | Crystallization temperature (° C.) | 88.4 | 89.4 | 89.0 | 84.6 | 90.0 | 94.2 | 110.9 | 118.1 | 89.2 | 89.5 | 102.1 |
|  | Transparency (%) | 84 | 87 | 89 | 86 | 88 | 92 | 75 | 57 | 91 | 90 | 83 |
|  | Flexibility (modulus: MPa) | 16.9 | 21.9 | 19.0 | 19.8 | 17.0 | 6.8 | 110.4 | 48.1 | 8.3 | 5.0 | 26.1 |
|  | Kink resistance (mm) | 21 | 29 | 23 | 22 | 23 | 27 | 58 | Unmeasurable | 20 | 19 | 23 |
|  | Clamp resistance (second(s)) | 980 | 410 | 520 | 84 | 1,150 | >1,200 | 1 | Unmeasurable | >1,200 | 810 | 54 |

TABLE 2-continued

|  | Comparative Example | | | | | | | | | | Reference |
|---|---|---|---|---|---|---|---|---|---|---|---|
|  | 1 | 2 | 3 | 4 | 5 | 6 | 7 | 8 | 9 | 10 | Example 1 |
| Anti-conglutination property | x | x | x | x | x | x | ○ | ○ | x | x | ○ |
| Solvent adhesion (N) | 31 | 23 | 35 | 22 | 30 | 30 | 4 | 35 | 30 | 33 | 48 |

*1: Hydrogenated styrene-based thermoplastic elastomer having a lower degree of vinylation It is found from Table 1 that the tubes made from the resin compositions produced in Examples 1 to 9 are excellent in all of transparency, flexibility, kink resistance, clamp resistance, anti-conglutination property, and solvent adhesion.

It is found that the tubes made from the resin compositions produced in Examples 7 to 9 in each of which any of the styrene-based thermoplastic elastomers (a-2 and a-3) containing styrene at 10 mass % or less is used are particularly excellent in kink resistance.

On the other hand, it is found from Table 2 that the tubes made from the resin compositions produced in Comparative Examples to 6 each have a ratio of diffraction peak intensities [I(14)/I(15)] of less than 1.4, and hence the tubes are poor in clamp resistance and anti-conglutination property.

It is found that the tube made from the resin composition produced in Comparative Example 7 is poor in kink resistance. Further, the tube is also poor in transparency, flexibility, and solvent adhesion.

Meanwhile, the tube made from the resin composition produced in Comparative Example 8 lost its tube shape before being formed into a circular shape, and hence its kink resistance could not be measured. Further, when the tube was clamped with a clamp, followed by removal of the clamp, the deformed shape of the tube was kept, or the tube partially broke, and hence its clamp resistance could not be measured. It is found from the facts described above that the tube produced in Comparative Example 8 is poor in kink resistance and clamp resistance and is remarkably poor in transparency.

The tubes made from the resin compositions produced in Comparative Examples 9 and 10 each contain a paraffin-based oil as a softening agent, and hence the conglutination property of the surface of each of the tubes is high and the clamp resistance is remarkably poor.

The tube made from the resin composition produced in Reference Example 1 is excellent in kink resistance, clamp resistance, and anti-conglutination property, but is slightly poor in transparency and flexibility.

TABLE 3

|  |  | Example | | Reference Example | | Comparative Example | |
|---|---|---|---|---|---|---|---|
|  |  | 10 | 11 | 2 | 3 | 11 | 12 |
| Resin composition/ | Thermoplastic elastomer (a) | | | | | | |
| parts by mass | a-1 | | | 60 | | 60 | |
|  | a-2 | 60 | | | | | |
|  | a-3 | | 60 | | | | |
|  | a-4 | | | | | | 60 |
|  | a-5 | | | | 60 | | |

TABLE 3-continued

|  |  | Example | | Reference Example | | Comparative Example | |
|---|---|---|---|---|---|---|---|
|  |  | 10 | 11 | 2 | 3 | 11 | 12 |
| | Polypropylene-based resin (b) | | | | | | |
| | b-1 (MFR = 25 g/10 minutes) | 40 | 40 | 40 | 40 | | |
| | b-3 (MFR = 7 g/10 minutes) | | | | | 40 | 40 |
| | Forming condition | C | C | C | C | C | C |
| Physical properties | Transparency (%) | 86 | 90 | 92 | 87 | 85 | 89 |
| | Kink resistance (mm) | 18 | 18 | 27 | 27 | 26 | 31 |
| | Clamp resistance (second(s)) | 1 | 4 | 2 | 1 | 723 | 270 |
| | Anti-conglutination property | ○ | ○ | ○ | ○ | x | x |
| | Solvent adhesion (N) | 46 | 38 | 40 | 39 | 40 | 54 |

Forming condition C: 175° C., 20 m/min

Table 3 shows that the tubes formed from the resin compositions produced in Examples 10 and 11 under the forming condition C are excellent in transparency, flexibility, clamp resistance, anti-conglutination property, and solvent adhesion. Besides, each of the tubes is particularly excellent in kink resistance and has kink resistance comparable to that shown in Examples 7 and 8 in Table 1.

On the other hand, when Reference Example 2 and Examples 1 and 3 in Table 1, Reference Example 3 and Example 5, Comparative Example 11 and Comparative Examples 1 and 3, and Comparative Example 12 and Comparative Example 2, are compared, respectively, it is found that the kink resistance of each of the tubes produced in Reference Examples 2 and 3 and Comparative Examples 11 and 12 is remarkably low.

INDUSTRIAL APPLICABILITY

The tube of the present invention has good transparency, flexibility, and solvent adhesion, and also has excellent clamp resistance, anti-conglutination property, and kink resistance. Thus, the tube of the present invention can be suitably used for medical devices which are used at the time of infusion, blood transfusion, peritoneal dialysis, catheter treatment, and the like. Besides, the tube of the present invention can also be widely used, in addition to medical application, as a tube used in fields in which a tube is required to have excellent flexibility and transparency, such as a tube for transporting food, which is used at the time of producing food and beverage or at the time of transporting beverage or the like in a vending machine, a tube for an electric appliance part, which is used at the time of supplying or discharging water or the like in an electric appliance, and an industrial tube, which is used at the time of washing automobiles or the like.

The invention claimed is:
1. A tube composed of a resin composition comprising:
a styrene thermoplastic elastomer (a) and
a polypropylene resin (b) that has a melt flow rate of 15 to 50 g/10 minutes at a temperature of 230° C. and at a load of 21.2 N,
wherein a mass ratio (a)/(b) of the styrene thermoplastic elastomer (a) to the polypropylene resin (b) is 90/10 to 40/60;
wherein the styrene thermoplastic elastomer (a) is a hydrogenated block copolymer prepared by hydrogenating a block copolymer comprising polymer block(s) (A), wherein in polymerized form polymer block(s) (A) comprises at least an aromatic vinyl unit, and wherein a total content of polymer block(s) (A) in the styrene thermoplastic elastomer (a) before hydrogenation is 5 to 40 mass % with respect to a total amount of the styrene thermoplastic elastomer (a); and a polymer block (B) that has a hydrogenation ratio of 70% or more, that comprises a 1,2-bond and a 3,4-bond at a content of 30 to 85 mol %, and that in polymerized form comprises at least one unit selected from the group consisting of isoprene and 1,3-butadiene;
wherein said resin does not contain a softening agent; and
wherein the tube has a ratio I(14)/I(15) of a diffraction peak intensity [I(14)] at a scattering angle (2θ) of 14° to a diffraction peak intensity [I(15)] at a scattering angle (2θ) of 15° of 1.7 or more in wide-angle X-ray diffraction.

2. The tube of claim 1, wherein the content of aromatic vinyl unit in polymer block(s) (A) is 80% by mass or more with respect to the mass of polymer block(s) (A).

3. The tube of claim 1, wherein the content of aromatic vinyl unit in polymer block(s) (A) is 90% by mass or more with respect to the mass of polymer block(s) (A).

4. The tube of claim 1, wherein the content of aromatic vinyl unit in polymer block(s) (A) is 100% by mass or more with respect to the mass of polymer block(s) (A).

5. The tube of claim 1, wherein the content of an isoprene unit and/or 1,3-butadiene unit in polymer block (B) is 80% by mass or more with respect to the mass of polymer block (B).

6. The tube of claim 1, wherein the content of an isoprene unit and/or 1,3-butadiene unit in polymer block (B) is 90% by mass or more with respect to the mass of polymer block (B).

7. The tube of claim 1, wherein the content of an isoprene unit and/or 1,3-butadiene unit in polymer block (B) is 100% by mass or more with respect to the mass of polymer block (B).

8. The tube of claim 1, wherein the hydrogenation ratio in polymer block (B) is 80% or more.

9. The tube of claim 1, wherein the hydrogenation ratio in polymer block (B) is 85% or more.

10. The tube of claim 1, wherein the glass transition temperature of polymer block (B) ranges from −50 to 30° C.

11. The tube of claim 1, wherein the glass transition temperature of polymer block (B) ranges from −45 to 10° C.

12. The tube of claim 1, wherein the glass transition temperature of polymer block (B) ranges from −40 to 0° C.

13. The tube of claim 1, wherein bonding between polymer block(s) (A) and polymer block (B) is linear, branched, radial, or a combination thereof.

14. The tube of claim 1, wherein the content of polymer block(s) (A) in styrene-based thermoplastic elastomer (a) before hydrogenation ranges from 5 to 30% by mass.

15. The tube of claim 1, wherein the content of polymer block(s) (A) in styrene-based thermoplastic elastomer (a) before hydrogenation ranges from 5 to 20% by mass.

16. The tube of claim 1, wherein the content of polymer block(s) (A) in styrene-based thermoplastic elastomer (a) before hydrogenation ranges from 5 to 10% by mass.

17. The tube of claim 1, wherein the weight average molecular weight of styrene-based thermoplastic elastomer (a) ranges from 4,000 to 500,000.

18. The tube of claim 1, wherein the weight average molecular weight of styrene-based thermoplastic elastomer (a) ranges from 30,000 to 300,000.

19. The tube of claim 1, wherein the weight average molecular weight of styrene-based thermoplastic elastomer (a) ranges from 50,000 to 250,000.

20. The tube of claim 1, wherein the polypropylene resin (b) has a melt flow rate of 20 to 50 g/10 minutes at a temperature of 230° C. and at a load of 21.2 N.

21. The tube of claim 1 that has a crystallization temperature of 95° C. or more at a cooling speed of 10° C./minute when the crystallization temperature is measured with a differential scanning calorimeter.

22. The tube of claim 1, wherein content of the 1,2-bond and the 3,4-bond in the polymer block (B) is in a range of 45 to 80 mol % with respect to a structural unit derived from the at least one compound in the polymer block (B).

23. The tube of claim 1, wherein content of the 1,2-bond and the 3,4-bond in the polymer block (B) is, with respect to a structural unit derived from the at least one compound in the polymer block (B), in a range of 55 to 70 mol %.

24. The tube of claim 1 that has a ratio I(4)/I(15) of diffraction peak intensity [I(14)] at a scattering angle (2θ) of 14° to a diffraction peak intensity [I(15)] at a scattering angle (2θ) of 15° of 2.25 or more in wide-angle X-ray diffraction.

25. The tube of claim 1, wherein a mass ratio (a)/(b) of the styrene thermoplastic elastomer (a) to the polypropylene resin (b) is 80/20 to 45/55.

26. The tube of claim 1, wherein a mass ratio (a)/(b) of the styrene thermoplastic elastomer (a) to the polypropylene resin (b) is 70/30 to 50/50.

27. The tube of claim 1, wherein said resin contains at least one of a tackifying resin, an inorganic filler or a lubricant.

28. The tube of claim 1 that is formed by melting said resin, forming the molten composition into a product having a tube shape through a die, followed by water cooling or air cooling, thereby yielding a tube.

29. The tube of claim 1 made by forming said resin composition into a tube directly with an extruder at the time of producing the resin composition.

30. The tube of claim 1 that has a crystallinity ranging from 14.0 to 22.4.

31. The tube of claim 1 that has a transparency ranging from 81 to 91% transmittance.

32. The tube of claim 1 that has a flexibility ranging from 14.8 to 22.8 MPa.

33. The tube of claim 1 that has a kink resistance ranging from 16 to 25 mm.

34. The tube of claim 1 that has a clamp resistance ranging from 1 to 40 secs.

35. The tube of claim 1 that exhibits no conglutination after being stacking and fixed with tape, being placed in a hot air drier at 100° C. for 30 mins, and being cooled at room temperature.

36. The tube of claim 1 that has a solvent adhesion ranging from 21 N to 45 N.

37. The tube of claim 1 that has a cross-section that has a circular shape or an elliptical shape.

38. The tube of claim 1 that has an outer diameter ranging from 1 to 50 mm.

39. The tube of claim 1 that has a thickness ranging from 0.3 to 30 mm.

40. The tube of claim 1 that is a multilayered tube.

41. A medical device comprising the tube of claim 1.

42. An infusion device, a blood transfusion device, a peritoneal dialysis device, a catheter, a tube for an infusion bag, a tube for a blood bag, a blood vessel prosthesis, a blood circuit, a syringe, a hemodialyzer, a blood component separator or an oxygenator comprising the tube of claim 1.

* * * * *